(12) United States Patent
Schiefer et al.

(10) Patent No.: US 6,570,655 B1
(45) Date of Patent: May 27, 2003

(54) PROCESS AND APPARATUS FOR MEASURING THE OPACITY IN GASES

(75) Inventors: Erich Schiefer, Graz (AT); Wolfgang Schindler, Graz (AT)

(73) Assignee: AVL List GmbH, Graz (AT)

( * ) Notice: Subject to any disclaimer, the term of this patent is extended or adjusted under 35 U.S.C. 154(b) by 128 days.

(21) Appl. No.: 09/721,693

(22) Filed: Nov. 24, 2000

(30) Foreign Application Priority Data

Nov. 26, 1999 (AT) .............................................. 2009/99

(51) Int. Cl.⁷ ................................................ G01N 21/59
(52) U.S. Cl. ........................ 356/437; 356/409; 356/419
(58) Field of Search ................................. 356/437, 336, 356/338, 340, 436–440, 405, 409, 419; 250/564, 573, 574, 575, 338.5, 339.13, 343

(56) References Cited

U.S. PATENT DOCUMENTS

| 4,518,861 A | 5/1985 | Krempl et al. |
| 4,525,627 A | 6/1985 | Krempl et al. |
| 4,577,105 A | 3/1986 | Kempl et al. |
| 4,737,652 A | 4/1988 | Faschingleitner et al. |
| 4,771,176 A | 9/1988 | Schiefer et al. |
| 4,953,390 A | 9/1990 | Krempl et al. |
| 5,243,847 A | 9/1993 | Engeljehringer et al. |
| 5,451,787 A * | 9/1995 | Taylor ..................... 250/338.5 |
| 5,831,730 A * | 11/1998 | Traina et al. ............... 250/564 |
| 6,025,920 A * | 2/2000 | Dec ........................... 250/573 |

FOREIGN PATENT DOCUMENTS

| DE | OS 25 57 268 | 6/1977 |
| EP | 0 094 374 | 11/1983 |
| EP | 0 123 458 | 10/1984 |
| EP | 0 616 205 | 9/1994 |
| WO | WO 93/06457 | 4/1993 |

* cited by examiner

Primary Examiner—Bruce Anderson
Assistant Examiner—Zia R. Hashmi
(74) Attorney, Agent, or Firm—Sonnenschein Nath & Rosenthal

(57) ABSTRACT

A process is provided for measuring the opacity in gases, especially in exhaust gases or in the atmosphere, at or near the maximum of the eye sensitivity in the green wavelength range with a central wavelength lying between 550 and 570 nm. In order, in a simple manner, to separately determine the components which are responsible for clouding in the visible wavelength range, or to make a correction possible by taking into consideration further components that have an effect in the visible range, the opacity in at least one second wavelength range which is located in the spectral between 200 nm and $2\mu$, and which overlaps at most slightly with the first wavelength range is additionally measured.

19 Claims, 4 Drawing Sheets

PROCESS AND APPARATUS FOR MEASURING THE OPACITY IN GASES

BACKGROUND OF THE INVENTION

The invention relates to a process for measuring the opacity in gases, especially in exhaust gases or in the atmosphere, at or near the maximum of eye sensitivity in the green wavelength range with a central wavelength range between 550 and 570 nm, as well as a device for measuring the opacity in gases, especially in exhaust gases or in the atmosphere, which device is equipped with an optical filter arrangement for the visible green spectral range at or near the maximum of eye sensitivity within a wavelength range from 550 to 570 nm in the beam path in front of at least one optical detector, and which is connectable with or is provided with an evaluating electronic system.

In opacity meters, at present, according to law or standards, measuring is done with a wavelength in the "green spectral range", at a peak wavelength of 550 to 570 nm and with a cutoff of less than 4% of the peak-value sensitivity of the peak wavelength for transmissions below 420 nm and above 680 nm. The opacity is defined there as measurement of the "clouding in the visible spectral range of the human eye sensitivity". The measurement in this spectral range of the "eye sensitivity" is knowingly so chosen that thereby the clouding of the atmosphere or "smog formation", caused by emissions should be checked. Alternatively, very often also the "k-value" in this spectral range is used as measure for the clouding, in which case the two values are reconvertible into one another by the Lambert Beer law:

100-opacity=100*EXP(-k*L), with L=measuring cell length, or measuring path length.

Mainly the "black" soot particles are/were caught by the opacity measurement and at present, in the legislation and the legally prescribed tests, it is assumed that the clouding or the k-value in the green spectral range is caused only by soot particles. In the opacity meters in use at present, with the measurement of the opacity in the "visible spectral range" at only one defined wavelength, it is not possible to distinguish whether the measurement value "opacity" or k-value (in $m^{-1}$) is really caused by soot, or not also by other exhaust gas components.

In motors, however, in reality there can occur also potential exhaust gas components (for example some nitrogen compounds, especially $NO_2$) which likewise absorb in this spectral range, and that can bring about a clouding. These additional components are wrongly included as "soot" in measurements made with the conventional opacity meter systems. In motor designs which were used in earlier years the dominant constituent causing the opacity really was the soot emission; this, however, is no longer valid for the present and future generations of motors.

In modem motor designs, for example those with CRT (Continuous Regenerating Type) exhaust gas treatment, soot particles are largely catalytically oxidized; on the other hand, however, a part of the NO concentrations present in the exhaust gas is transformed into $NO_2$ by these catalytic processes. $NO_2$, however, is a gas component which is likewise absorbed in the green opacity meter spectral range, and is concurrently measured as "soot". On the other hand, "white", nonabsorbing particles can also occur (for example sulfates with agglomerated water or also other particle-form reacting products such as condensing hydrocarbons), which by weakening of the light in consequence of a light scattering can likewise have an effect on the measuring.

Likewise with the measuring apparatuses which measure in the middle IR-range, such a discrimination cannot be carried out, especially not for sulfates and for $NO_2$. It is not possible to measure $NO_2$ in motor exhaust gases by means of IR absorption through cross-sensitivity with the steam that is present in the exhaust gas, and neither can the water be removed for this measurement by means of a gas cooling, since $NO_2$ that is soluble in water is simultaneously removed along with it. The measurement of the $NO_2$ concentration can occur at present only by chemo-luminescnce detectors (CLD), and there, however, also only indirectly by means of a difference measurement ($NO_x$–NO=$NO_2$).

For similar reasons sulfate particles in the IR range likewise cannot be measured; especially a direct measurement of the opacity constituent resulting from the light scattering of the sulfate particles is not possible in the visible spectral range. The same holds also for the opacity caused by non-absorbing but condensed, and therewith likewise light-scattering, HC particle constituents.

All concepts in effect at present in the IR range for the total particle measurement are based on measurements of the HC total concentrations (as gas or as gas+particles) and on back-reckoning models (thus also are the examples in EP 0 094 374 and EP 0 123 458). Some of the concepts at present on hand for the HC particle calculation are based on complicated measurements at different temperatures, on the filtering of the gas, on measurement of the "gaseous " HC concentration present, and on a back calculation of the particle constituents, as represented in EP 0 616 205.

A direct measurement of the "clouding" by the light scattering, which is still definitive for the visible green spectral range is, for physical reasons, not possible in the IR range, since through the proportionality of the effect to the 4th power of the ratio of light wave length to particle size, factually no light scattering for particles from motor exhaust gases is present in the IR range.

A back calculation such as theoretically might be possible at least in measurements of the total absorption spectra of the exhaust gas in IR (NIR to FIR),with rapid and high-resolving FTIR systems which, however, are extremely costly and expensive, even for $NO_2$, ultimately fails on the fact that the momentary dynamic relations, which occur in the free acceleration and that certainly definitively influence the momentary particle composition, cannot be recalculated from the data obtained. The same holds also for measurements with laser diodes, such as are described, say, in EP 0 920 285, in which there, too, only soot and HC are measured.

Because of the great differences among the "middle IR" wavelength ranges, all of the present-day methods are completely incapable to describe, or can describe only very incompletely, the conditions present in the visible spectral range. In DE 25 57 268 there is described a process for extinction measurement which can be used, for example, for the determination of the smoke density in smokestacks, but also for the measurement of the dust concentration in work-places, of the emission in the lime works environment, as well as for the determination of the visibility range in fog on highways and at airports. There, by extinction measurements at two different wavelengths, a distinction can be made possible between absorbing and non-absorbing particles, primarily between soot or aerosol particles and vapor-form water. It is not determined, however, in what manner and to what extent an opacity in a certain wavelength range affects the value for the opacity in another wavelength range.

SUMMARY OF THE INVENTION

The problem of the present invention, therefore, was to find a process which in a simple manner, and avoiding the above-described disadvantages of the state of the art, makes it possible separately to determine the components which are responsible for the clouding in the visible wavelength range and which, for the measurement of opacity on the basis of soot particles, permits a correction by consideration of further components having an effect in the visible range. A further problem was a device for the execution of the process.

For the solution of the above problem the process mentioned at the outset is characterized in that the opacity, additionally, is also measured in at least one second wavelength range which is located in the spectral range between 200 nm to $2\mu$, and which at best slightly overlaps the first wavelength range. The invention is based on the principle that it was surprisingly ascertained that through the use of at least one additional color filter and therewith measurement in a further wavelength range it is possible to distinguish what share of the measured opacity (or of the k-value) is caused by the soot particles, for example, and what share is caused by other components, for example by scattered light of extremely small, non-absorbing particles and/or by other light-absorbing gas components such as $NO_2$.

According to a further feature of the invention it is provided that the measurement values of at least one additionally used wavelength range are automatically compared with the measurement value of the green wavelength range, and that from these a correction is calculated for the measurement value in the green wavelength range.

Advantageously also, the signals of all the wavelength ranges used can be automatically compared with one another, and from this there is automatically determined the signal share of at least one further component that contributes to the opacity in the green wavelength range.

If, according to a further feature of the invention, at least one additional measurement is taken in a range with a central wavelength between 300 and 450 nm, it is possible to ascertain or to calculate the share of the measured opacity (or of the k-value) which is caused in the green light spectral range by "white" scattering particles. This is possible since it was recognized that for the k-value the effects of the light scattering on small particles are proportional to the $4^{th}$ power of the light wavelength, while the effect of the soot absorption is linearly dependent on the wavelength of the filter.

If, alternatively or additionally to this there still is performed an additional measurement in a range the central wavelength of which ranges between 600 nm and $2\mu$, there can be determined therewith the contribution of most gas components which likewise have a measuring effect on the green spectral range, and the signal share caused by the scattered light can be determined, so that these shares can be taken into account for the correction of the measurement value in the visible range, and the contribution of the "soot" can be determined appreciably more accurately.

Preferably, the central wavelength of the additional measurement, there, lies in the range between 600 nm and $1.2\mu$.

According to a further feature of the invention it is provided that the measurements in the various wavelength ranges are executed automatically controlled in succession, so that a manual intervention is avoided and the measuring series is feasible rapidly and simply.

Still more rapidly, even though with somewhat higher expenditure in apparatus, the process of the invention can be carried out according to one of the preceding paragraphs when the measurements are simultaneously carried out in all wavelength ranges.

The device described at the outset for the execution of the process of the invention is characterized for the solution of the problem posed in that additionally at least one second optical filtering arrangement is provided for a second wavelength range the central wavelength of which is located in the spectral range between 200 nm to $2\mu$, and which overlaps at best slightly with the first wavelength range.

Advantageously the device according to the invention is characterized in that the evaluating electronic element is provided with a circuit or a program which automatically asks for the measurement values, and from them automatically calculates a correction for the measurement value in the green wavelength range.

According to a further inventive feature the evaluating electronic element can be provided with a circuit or a program which asks for the measurement values in all the wavelength ranges used and from them automatically calculates values in order to distinguish the signal shares of at least one component responsible for the opacity in the green wavelength range, from other components likewise absorbing in this wavelength range.

In order to determine the share of the measured opacity (or of the k-value) which is brought about by "white" scattering particles, according to a further feature of the invention there is provided at least one additional optical filtering arrangement for a wavelength range the central wavelength of which falls in the range between 300 and 450 nm.

On the other hand, also additionally, or alternatively, to the feature just mentioned, at least one additional optical filtering arrangement can be provided for a wavelength range the central wavelength of which falls in the range between 600 nm, and $2\mu$, whereby then the contribution of most gas components in the green spectral range and also the contribution of the scatter light in the green spectral range can be determined and used for the correction of the measurement value on the contribution brought about by the soot.

Preferably it is provided there that the additional optical filter arrangement is for a wavelength range the central wavelength of which falls between 600 nm and $1.2\mu$.

A manual operation is avoided if pushers, swinging arms, turnable disks or the like that carry the optical filter arrangements for the gliding-in or swinging-in of the, or of all optical filter arrangements are provided in the beam path, in front of the detector. Therewith the measuring process is entirely automatable and also more is simply and rapidly feasible than by hand.

Advantageously for a compact and simple construction it can be provided that a blind with openings movable in front of the detector is provided, in which openings the optical filter arrangements are installed.

There preferably for the fully automatic operation of the device there is provided a drive arrangement for the blind and this is connected with the evaluating electronic element. On the other hand, according to a further feature of the invention it can be provided that several detectors are provided parallel and are connected in common with an evaluating electronic element, in which case in front of each detector in the beam path there is provided in each case an optical filter element. Therewith the measurement is more rapidly practicable, so that also rapidly changing relations can be followed in real time.

In the following specification the invention is to be further explained with the aid of a preferred example of execution for the soot particle measurement.

It was possible to establish that especially with modern motor designs certainly a definite share of the "opacity" can come about by other components besides soot particles, namely especially by $NO_2$, but also in part by "transparent" non-absorbing particles, such as sulfates and water deposited on these sulfate particles.

It was ascertained, surprisingly, that through the use of at least one further "optical filter" in the visible spectral range or also in the near infrared up to maximally ca. $2\mu$, the shares of the measuring value in the green spectral range caused by these components, i.e., the total measured opacity, can be determined and therewith the "opacity" measured in the green spectral range can be selectively separated into the shares which are brought about by $NO_2$ and by "sulfates or also other condensed HC-particles".

There it is of special significance that through this inventive type of measuring in the visible—not in the middle infrared—spectral range for the first time there exists the possibility of selecting the component $NO_2$ an the share of opacity (or of the k-value) caused by the clouding of $NO_2$ in the green "opacity spectral range", and also additionally to measure the contributions of sulfate particles (and also of the non-absorbing HC particles) in this spectral range. Therewith, however, for the first time it is furthermore directly possible to measure the concentration of $NO_2$ when the measuring system is calibrated by means of an $NO_2$ calibrating gas.

Further, the new invention offers the possibility, also for future exhaust gas tests, separately and highly dynamically to check the share of the soot component and simultaneously the share of $NO_2$ emitted in the free acceleration of motors. In normal idling-measurements or in measurements made with the presently available opacity-meters, the $NO_2$ ejection cannot be measured. The testing of vehicles or motor is therefore substantially simpler to carry out with the process of the invention and the corresponding device as well as of the method used for the evaluation.

A further not-to-be-neglected advantage of this invention is also to be seen in that the concept it uses, in comparison to other measuring concepts such as FTIR or MID NDIR, or laser-diodes measurements, is substantially more economical and simpler to implement and, in addition, the usual sturdy hardware designs can be used for the opacity measuring apparatuses (full current to partial current). The background is that the soot particles absorb strongly and through their usual size distribution the concentration-proportional k-value of the soot particles depends linearly on the light wavelength. On the other hand, most gas components which can affect the measurements in the green spectral range, in the "red" visible spectral range" as well as also near the IR range, no longer absorb, or at least do so substantially less; likewise in the red spectral range the effects through the scattered light become appreciably less or are negligible, so that only "soot" continues to be measured there and, through following the accepted forms, the shares are separately measurable.

In the event that a substantial share of the measured opacity (or of the k-value) in the green spectral range is caused by "white" scattering particles, the use of an alternative or additional filter in the "blue or near UV range" likewise permits to discriminate among the effect they cause. The effects brought about by the scattering of light on small particles are proportional to the 4th power of the light wavelength, while, as already mentioned above, the effect caused by the soot absorption is linearly dependent on the wavelength of the filter.

The measurement of the different component shares, therefore, can occur by the means that the green filter of the measuring apparatus on the one hand, for example manually by a pusher or also automatically, is replaced by a filter in the blue spectral range (or in the near UV-range). Alternatively also two or even several detectors can be simultaneously equipped with different filters, or the filters can be brought into the beam path in succession, for example by a chopper wheel. Therewith the measurement can occur simultaneously in all wavelength ranges or at least rapidly in one range after another.

In the first case the evaluation must occur either externally after the measuring or also, preferably program-controlled, internally. Altogether, the first-described variant is suited for long-durational constant measurements, while for rapid dynamic measuring processes, the second alternative must be used.

Therewith from the two or three measurement values, by diverse conversion algorithms there can be selectively measured the absorption shares caused by soot or also by other components in the green, standardized spectral range. The concentration, the k-value share or also the contribution to the opacity which is caused by the other absorbing components, such as, for example, $NO_2$ and by light-scattering particles, therefore, can additionally be determined. By this measuring principle and evaluation it is thus possible to distinguished what share of the opacity or of the k-value brought about in the green spectral range is caused by soot, by a gas such as $NO_2$, or by scattering particles such as sulfates or HCs. There can also be calibrated and calculated, furthermore, the concentrations of the gaseous components. From the corrected opacity or k-value for "soot" there can likewise be calculated or measured its true concentration, since the k-value is directly proportional to the concentration of soot. The determination of the sulfate- or HC-particle shares can occur likewise with this method, at least roughly, there being selectively calculable, here, only the concentrations accumulating as particles. By the variation in the size distribution of the purely scattering particles that are present, the measuring accuracy of the concentration calculation is possible only restrictedly. The measuring or calculating accuracy of the share caused by these particles in the different spectral ranges, however, is not thereby restricted.

With use of three filters in the presence of three components to be considered, or of two filters with the presence of only two components, therewith there is also possible a calculation of the concentration.

In order to avoid possible cross-sensitivities the, additional spectral ranges especially in the near IR range, must be chosen in such manner that no absorptions or only the most minimal absorptions or measuring effects are caused by the water vapor- or $CO_2$-content in the measuring gas.

BRIEF DESCRIPTION OF THE DRAWINGS

Such a calculation example for measurement and evaluation is represented by way of example in the following, as is an example of execution of an apparatus according to the invention.

DETAILED DESCRIPTION OF THE PREFERRED EMBODIMENTS

Figure 1:
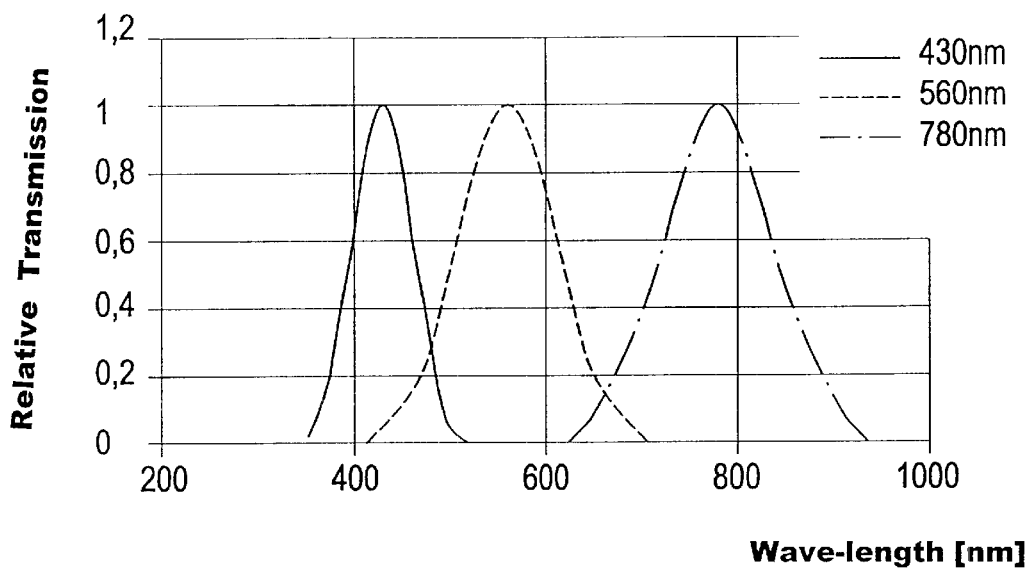
FIG. 1 shows the spectral sensitivity for an exemplary system with three filters in the measuring cell.
Figure 2:
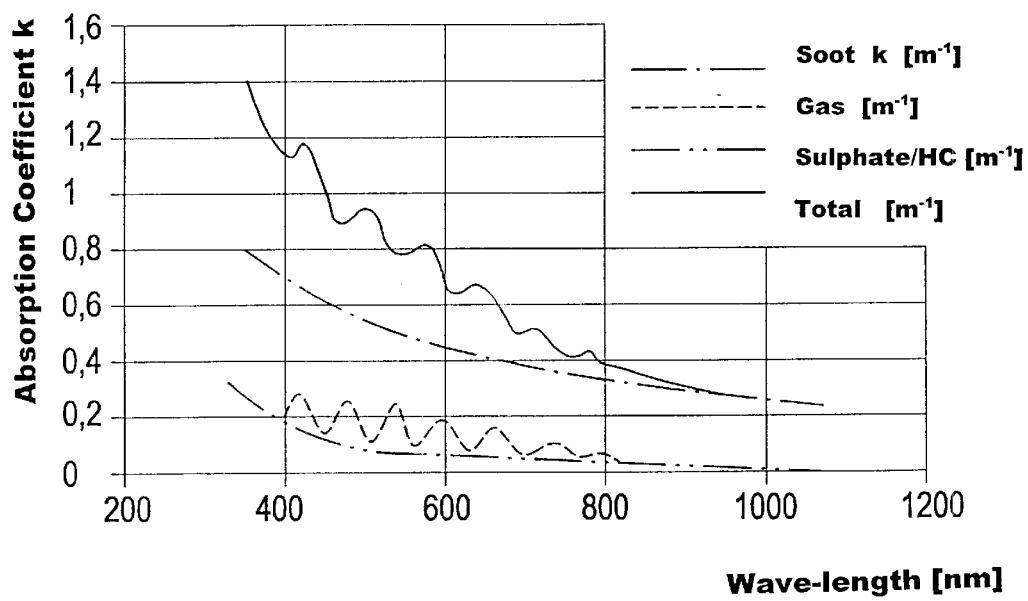
FIG. 2 shows spectrally resolved measurement values which are brought about by concentrations of soot, scattering particles and an absorbing gas.
Figure 3:
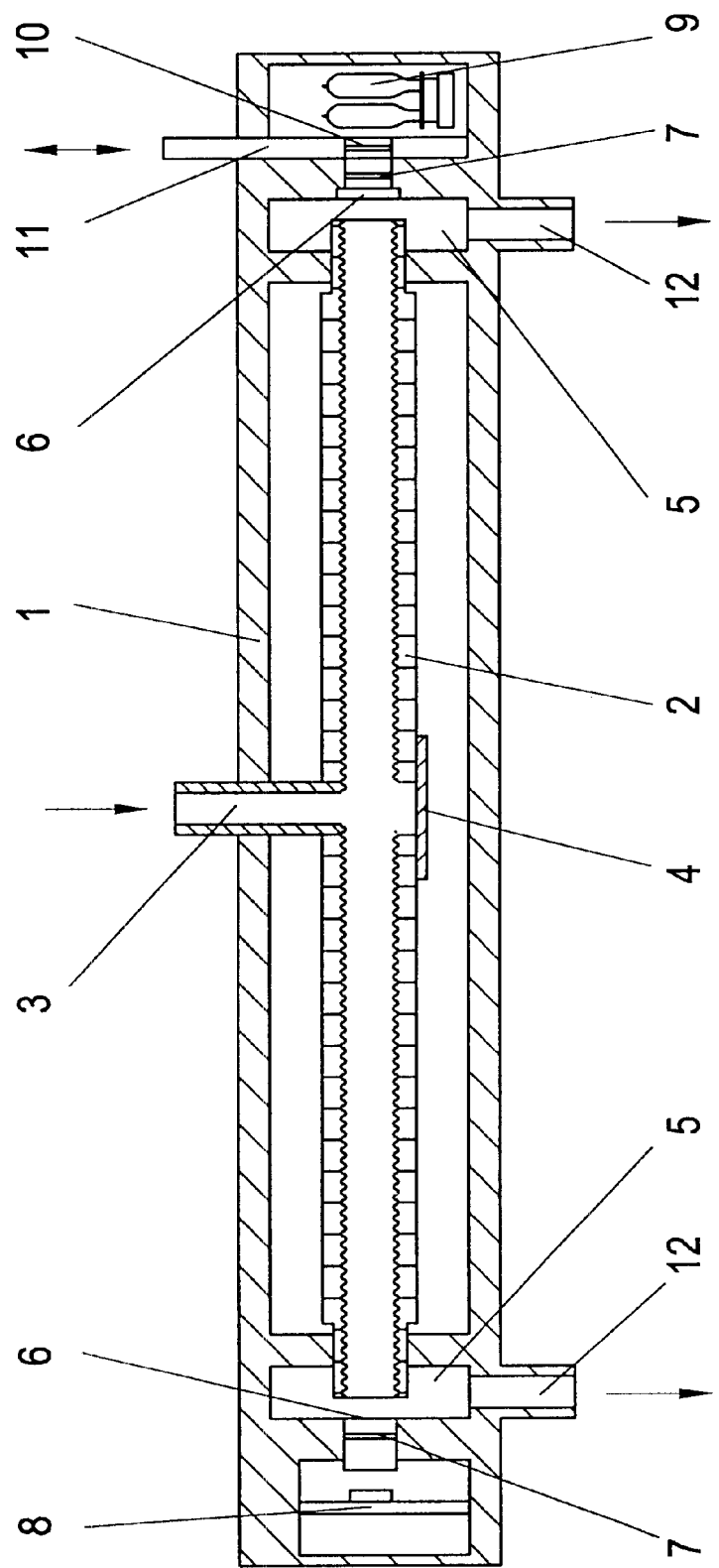
FIG. 3 is a schematic longitudinal section through an opacity meter according to the invention.

It is also possible to calibrate the system, for example, for the gas component $NO_2$ and it is therewith possible also to measure hydrodynamically emission value of $NO_2$ emitted in the acceleration phase, for example in the free acceleration, in addition to the soot emission value. The calculation of the individual concentrations of the different components, or their k-values, or opacities (at a certain wavelength) can occur by the use of standard mathematical matrix functions. For example, the case represented in the above FIGS. 1 and 2 for the three filters and the three components in the green spectral range, can be solved for the k-value, for example.

The k-values measured by the three different filters are multiplied with a transposed calibrating matrix, and from this it is possible to calculate the shares of the k-value caused by the individual components in the green spectral range. This calibrating matrix is yielded in part from the purely physical/mathematical relations for scattering and absorption. In the presence of nonlinear dependencies, as for gases, a calibration is possible.

Values (soot, gas, scattering particles)=transposed calibrating matrix*(measurement values filter 1, filter 2, filter 3)

The calibrating matrix is, in this case, a 3×3 matrix of the following type:

KR(F1) KR (F2) KR(F3)
KG(F1) KG(F2) KG(F3)
KS(F1) S(F2) KS(F3)

KR, KG, KS are calibrating factors for soot, gas and scattering particles.

F1, F2 and F3 represent the three filters.

Since the values in the calibrating matrix are functionally connected, at least in part, obviously also the k-values and/or the opacities and/or the concentrations can be calculated for the spectral ranges of the other filters or also for "theoretical filters", which were not used. Possible nonlinearity, however, must be taken into consideration in calculations.

Analogously the calibrating matrix is to be set up as a k-value matrix, since thereby the calibration of the measuring system, the separating into the different component shares, and the calculations of concentration, k-value, and opacity can be substantially simplified. The computing of opacity and concentration from the k-values can be done with the help of the Lambert-Beer law. There is also possible, to be sure, a calibrating matrix in opacity or concentration units; then, to be sure, the resulting calibrating matrix values are at least in part nonlinear functions of the individual component magnitudes and must be adapted iteratively in dependence on the measuring values themselves. Such a procedure requires unnecessary calibrating and computing expenditure.

An opacity meter according to the invention could be constructed, for example, as this is represented in FIGS. 3 to 7 and is explained in the following. In a housing or frame 1 there is borne a measuring tube 2. Into this measuring tube over a connection there is introduced the gas to be analyzed. Opposite the connection 3 there is advantageously provided a baffle plate 5. At both ends of the housing 1 there are provided outlet chambers 5, into which the measuring tube 2 issues, and which are closed off with respect to these orifices with heatable window elements 6 on one side now, preferably behind a blind 7, there is provided a detector unit with a detector 8 for the determination of the light of a lamp unit located at the opposite end of the measuring tube 2, and that crosses the measuring tube 2.

The lamp unit, likewise equipped with a blind 7, contains one or more lamps 9, preferably halogen lamps, as well as at least one further color filter 10, which is installed in a pusher 11 or similar unit, slidable preferably automatically in the beam path of the lamp unit.

The gas, after passing through the measuring tube 2 and the outlet chambers 5 leaves the apparatus over the outlet connections 12.

The filter inset 11 for the reception of the different measuring filters 10 in the at least two spectral ranges is accommodated by way of example on the side of the lamp unit, but alternatively, obviously, it can also be located on the detector side.

Figure 4:
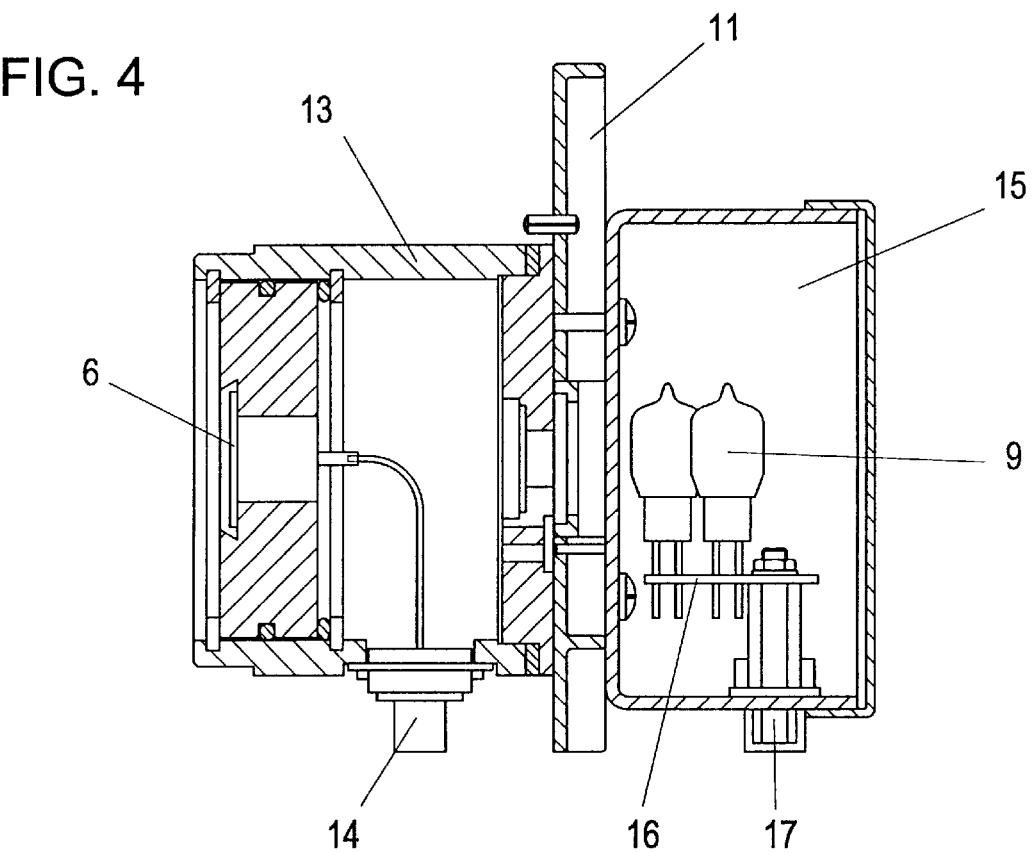
FIG. 4 is a longitudinal section through the lamp unit of FIG. 3 in larger scale.

In FIG. 4 there is represented an exemplary lamp unit in a larger scale. Between the window unit 13 for the window element 14, electrically heatable over the connecting sleeve 14, and the lamp housing 15, there is installed the automatically or manually actuatable pusher 11 (see also FIG. 6b) for the color filter. In the lamp housing 15 there are installed the support 16 for the halogen lamps 9 as well as the connecting sleeve 17 for its current supply. Instead of the filter inset 11 slidable in lengthwise direction there can also be used an arrangement with a rotating filter wheel 18 (see FIG. 6a), in which the filters 10 are installed.

Figure 7:
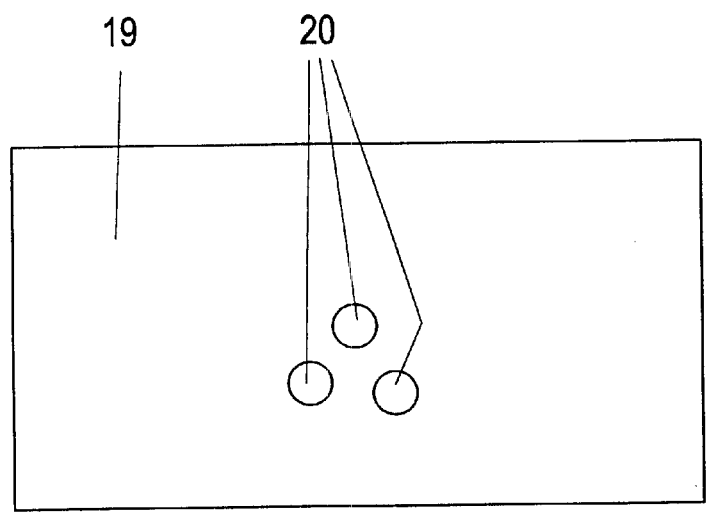
FIG. 7 is a plan view of a filter plate for such an opacity meter.

Another form of execution of the invention can provide that the detector unit is equipped with a detector plate 19 (see FIG. 7). On this plate 19 there can then be present several detectors 8, in front of which the color filters 10 are swingable into the beam path. There can also be provided, however, at least two separate detector-color filter units 20, in which in this case there can be used an arrangement without any filter inset 11 or filter wheel 18 of its own, which proves advantageous especially for hydrodynamic measurements with simultaneous measuring in all spectral ranges simultaneously.

Figure 5:
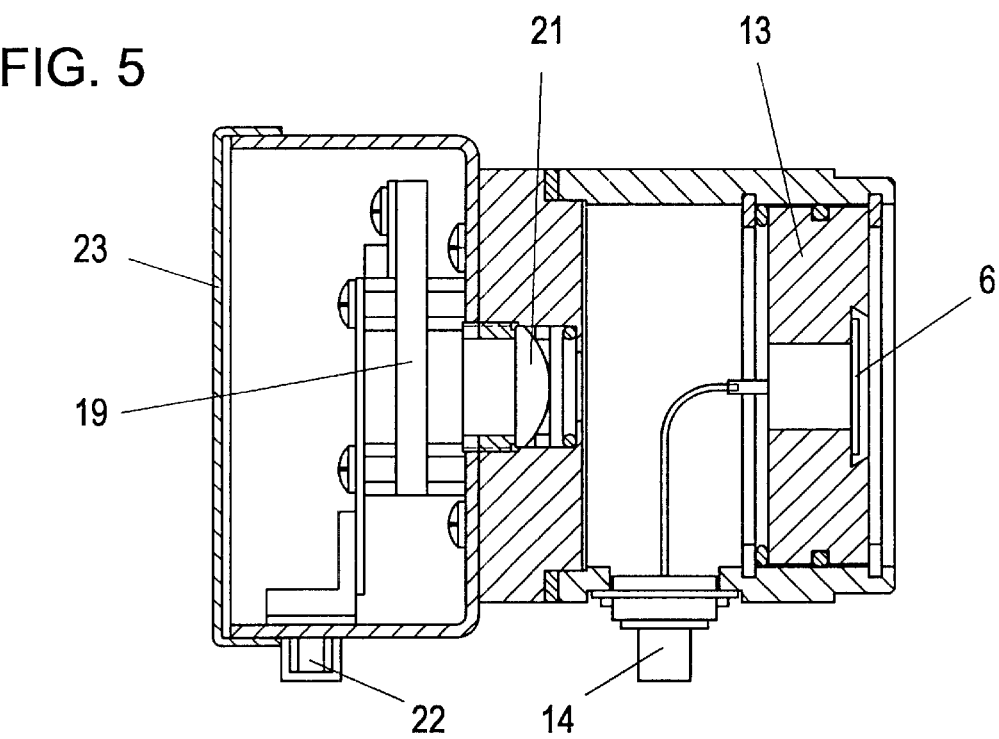
FIG. 5 shows an enlarged longitudinal section through the detector unit of FIG. 3.
Figure 6A:
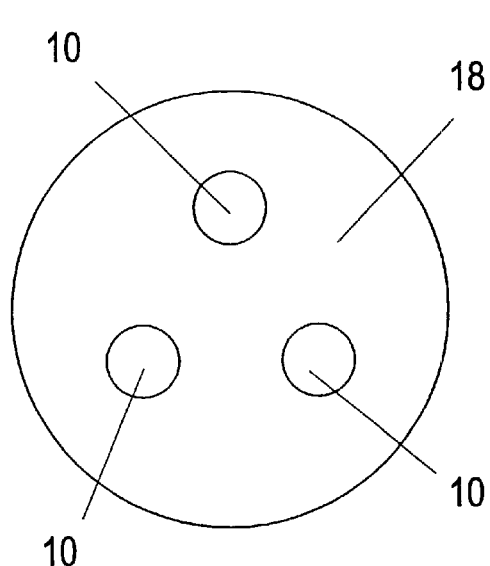
FIGS. 6a and 6b show in each case a plan view of a filter inset for an opacity meter according to the invention.
Figure 6B:
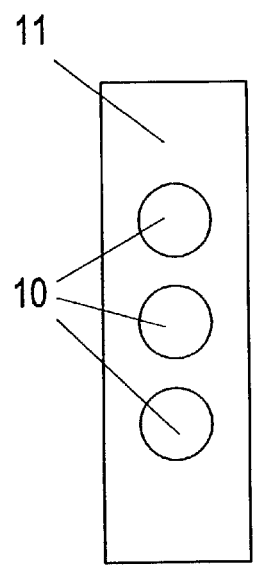

A detector unit with detector plate 19 is represented in a larger scale in FIG. 5. Behind the heatable window element 6 in the window unit 13 and a lens 21 there is mounted the detector plate 19 and the latter is connected with the current supply and the evaluating electronic element, over the connecting sleeve 22 and through the detector housing 23.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A process for measuring an opacity in gases near the maximum of eye sensitivity in a first, green wavelength range from 550 to 570 nm central wavelength, comprising the further step of additionally measuring the opacity in at least one wavelength range which lies in the spectral range between 200 nm and $2\mu$, and which overlaps at most only slightly with the first wavelength range.

2. A process according to claim 1, comprising the further step of automatically comparing measurement values of at least one additionally-used wavelength range with a measurement value of the green wavelength range, and from the comparison, calculating a correction for the measurement value in the green wavelength range.

3. A process according to claim 1, comprising the further step of automatically comparing signals of all the wavelength ranges with one another, and that from this comparison automatically determining a signal share of at least one further component that contributes to the opacity in the green wavelength range.

4. A process according to claim 1, wherein said step of additionally measuring occurs at least in one range, the central wavelength of which lies between 300 and 450 nm.

5. A process according to claim 1, wherein said step of additionally measuring occurs at least in one range, the central wavelength of which lies between 600 nm and $2\mu$.

6. A process according to claim 5, wherein said step of additionally measuring occurs at least in the range between 600 nm and $1.2\mu$.

7. A process according to claim 1, wherein the measurements in the different wavelength ranges are executed in succession, and are automatically controlled.

8. A process according to claim 1, wherein the measurements are performed simultaneously in all wavelength ranges.

9. A process according to claim 1, wherein the measurements are performed in one of exhaust gases and atmospheric gases.

10. A device for measuring an opacity in gases comprising a first optical filtering arrangement for the visible green spectral range at or near the maximum of eye-sensitivity with a central wavelength of between 550 to 570 nm lying in a beam path of at least one optical detector, an evaluating electronic element operatively connected with said first optical filtering arrangement and at least one second optical filter arrangement for a second wavelength range, a central wavelength of which is located in a spectral range between 200 nm and $2\mu$, and which at most overlaps only slightly with the first wavelength range.

11. A device according to claim 10, wherein the evaluating electronic element is provided with at least one of a circuit and a program which automatically obtains measurement values from the first optical filtering arrangement and the at least one second optical filter arrangement and from these measurement values automatically calculates a correction for the measurement value in the green wavelength range.

12. A device according to claim 10, wherein the evaluating electronic element is provided with at least one of a circuit and a program which automatically obtains measurement values in all wavelength ranges used, and from these measurement values automatically calculates values in order to distinguish signal shares of at least one component responsible for the opacity in the green wavelength range, from other components likewise absorbing in this wavelength range.

13. A device according to claim 10, wherein at least one additional optical filter arrangement is provided for a wavelength range, the central wavelength of which lies between 300 and 450 nm.

14. A device according to claim 10, wherein at least one additional filter arrangement is provided for a wavelength range, the central wavelength of which lies between 600 nm and $2\mu$.

15. A device according to claim 14, wherein in that at least one additional optical filter arrangement is provided for a wavelength range, the central wavelength of which lies between 600 nm and $1.2\mu$.

16. A device according to claim 10, wherein at least one of pushers, swinging arms and rotatable disks carrying the optical filter arrangements for the sliding-in or swinging-in of the optical filter arrangement or of all the optical filter arrangements, are provided in the beam path in front of the detector.

17. A device according to claim 16, wherein a blind with openings movable in front of the detector is provided, in which openings the optical filter arrangements are installed.

18. A device according to claim 17, wherein a drive arrangement is provided for the blind and is connected with the evaluating electronic element.

19. A device according to claim 10, wherein several detectors are provided in parallel and are connected with a common evaluating electronic element, wherein in a beam path in front of each detector there is provided in each case at least one optical filter arrangement.

* * * * *